United States Patent [19]

Nelson

[11] Patent Number: 4,839,171

[45] Date of Patent: Jun. 13, 1989

[54] COMPOSITION FOR TREATING IMPAIRED LACTATION

[75] Inventor: Martin J. Nelson, Waconia, Minn.

[73] Assignee: Techmix, Inc., Edina, Minn.

[21] Appl. No.: 20,085

[22] Filed: Feb. 27, 1987

Related U.S. Application Data

[63] Continuation of Ser. No. 676,555, Nov. 30, 1984, abandoned.

[51] Int. Cl.$^4$ .................. A61K 37/02; A61K 35/78; A23K 1/18
[52] U.S. Cl. .................. 424/101; 424/195.1; 514/2; 514/21; 514/892; 426/630; 426/647; 426/657; 426/807
[58] Field of Search .............. 424/195.1, 101; 514/2, 514/892; 426/630, 647, 657, 807

[56] References Cited

U.S. PATENT DOCUMENTS 4,225,620  9/1980  Rawlings et al. ............. 426/630
4,452,779  6/1984  Cockerill ...................... 424/128

OTHER PUBLICATIONS

Handbook of Non-Prescription Drugs 5th Ed., 1977, pp. 40, 41, 43–45, 53.
Practical Vet. Pharm., Milks, 1949, pp. 280–287, 298–301.

*Primary Examiner*—Johnnie R. Brown
*Assistant Examiner*—Jacqueline M. Stone
*Attorney, Agent, or Firm*—Peterson, Wicks, Nemer & Kamrath

[57] ABSTRACT

Composition for treating impaired lactation is described according to the preferred embodiment of the teachings of the present invention for oral administration to swine. The composition according to the teachings of the present invention includes blood albumin meal to provide a rich source of nutrients such as amino acids. Blood albuin helps insure that the osmotic pressure of the blood and interstitial tissue fluid around the mammary gland alveoli is optimized. Psyllium seed is further provided in the composition according to the teachings of the present invention as a natural laxative and as an effective aid in the treatment of constipation. Specifically, an oily, mucilaginous mass is formed when the psyllium seed comes in contact with water or fluid in the digestive tract and lubricates the digestive tract to help stimulate evacuations. The composition according to the teachings of the present invention includes an electrolyte base to help eliminate fluid and electrolyte imbalances in the tissues that may lead to excessive udder edema and caking. The treatment composition of the present invention provides a slow, gentle anticonstipating action in a palatable manner for maintaining a good appetite with less signs of constipation and for maintaining optimum milk production with less signs of udder edema and caking.

11 Claims, No Drawings

COMPOSITION FOR TREATING IMPAIRED LACTATION

BACKGROUND

The present invention relates generally to treatment compositions, particularly to oral treatment compositions, and specifically to oral treatment compositions for the treatment of impaired lactation.

The swine industry suffers severe continuous economic losses as a result of impaired lactation in recently postpartem gilts and sows. Sows or gilts that do not milk freely and abundantly after farrowing deprive their newly born piglets of adequate energy resources or nutrients for optimum growth and survival. The newly born piglet has very limited energy and nutrient reserves and requires nourishment within several hours after birth with continuous daily feedings every 2 to 4 hours for the first 10 to 14 days of life. Piglets not receiving adequate nourishment through continuous nursing become stunted in the first few days of life and are subject to increased mortality. Lack of adequate nourishment, as a result of total or partial agalactia on the part of the dam, leads to weakness and starvation in the nursing young that further predisposes the newly born piglet to stunting, disease and death. The mortality rate of nursing piglets from the time of birth until weaning or during the lactation period ranges between 25 to 30 percent of the pigs born. The primary contributing factor to this high mortality during nursing or the lactation period is due to lactation failure or agalactia.

There are many factors involved in milk production, such as genetics, nutrition, management, and disease. Good swine producers take special precaution to minimize the impact of these factors as they may be related to lactation failure. In addition to the above factors, the ingredients normally found in milk have a dramatic impact on lactation or milk flow.

Normal milk contains protein, fat, lactose, minerals-electrolytes, vitamins and water. Of these milk ingredients, lactose is considered to be the primary milk ingredient which controls the amount of milk that is produced by the mammary gland. The exact biological manner in which lactose controls milk production is not totally understood; however, the main mechanism of action is through its osmotic pressure action. The positive osmotic pressure of the blood and tissues surrounding the alveoli of the udder forces blood fluid into the secretory cells of the alveoli. These cells convert the blood fluids and nutrients into milk and push the milk into the alveolar cavities which are grape-like in structure. In the normal udder, oxytocin causes a contraction of the alveolar capsules which releases or lets down the milk to the nursing piglet. The emptied alveolar capsule has a negative osmotic pressure which then again stimulates milk formation and storage. This process is constantly repeated without interference in high producing sows and gilts.

To assure maximum milk volume production and free flow to the nursing piglets, proper osmotic pressures are essential throughout the lactating mammary gland. These osmotic pressures are controlled by lactose, protein, fat and electrolytes in the milk fluid. Milk lactose being the major osmotic factor in milk is most instrumental in governing milk production and milk flow. Any factors such as edema or caking which disturb the optimum osmotic pressures will predispose the gilt or sow to agalactia or lactation failure.

Lactation failure is a complex and complicated management problem in that it cannot be attributed to any one infectious agent or single management factor. The clinical picture may vary from a simple lack of mammary gland development with inadequate milk production to severe complications of the normal udder that somehow impede or restrict milk flow and release. In most cases of inadequate mammary gland development, the secretory cells of the mammary gland are too juvenile or non-functional in their ability to convert blood nutrients into milk. The main contributing factors to inadquate mammary gland development are thought to be nutritional, genetic or hormone related.

In sows or gilts with adequate mammary gland development, lactation failure or agalactia are usually due to complications that impede or inhibit the flow or release of milk to the nursing piglet. Complications which may restrict and impinge on normal milk flow are edema, persistent congestion and inflammation. When normal milk flow is restricted, the milk is retained in the alveoli and it sets up a chain reaction that interferes with continued milk production. The retained milk through its persistent osmotic pressure inhibits the conversion of blood sugar to milk sugar. In cases where the osmotic pressure is extreme, the milk fluids are actually reabsorbed and continued milk production is severely impaired which results in drying off or cessation of milk production.

Milk retained in the alveoli serves as a rich potential media for bacterial growth. Bacteria that find their way up the teat canal and into the alveoli, flourish in the nutrients of the retained milk. As the bacteria flourish, they produce toxins and inflame the tender mammary gland. When the condition persists for several hours, the udder becomes engorged, inflamed and non-functional. This condition has been recognized as lactation failure due to MMA or Mastitis—Mertritis—Agalactia.

For sows to maintain their optimum milk flow commencing at farrowing or birth until weaning, it is essential that the sows or gilts be fed a high-energy or caloric ration which can be readily digested and metabolized into utilizable blood glucose for conversion into milk nutrients such as lactose. As set forth hereinbefore, lactose is thought to be the major osmol in milk and is considered to be responsible for controlling the volume of milk secreted. It is essential that an adequate supply of glucose be available within the mammary secretory epithelial cell for the continued formation of lactose as there is a definite relationship between reduced or lowered blood glucose levels and reduced milk flow or agalactia in the sow or gilt.

One of the primary causes of agalactia and lactation failure is intestinal stasis or constipation. Many sows and gilts encounter this problem in the farrowing crate due to lack of exercise, poor appetite and changes in management and environment. Sows afflicted with constipation or intestinal stasis immediately after farrowing, encounter impaired digestion and energy utilization in a few hours if not corrected. Sows and gilts constipated for an extended period have poorer digestion and feed utilization which predisposes the sow or gilt to hypoglycemia or reduced blood sugar. The constipation, impaired digestion and altered metabolism lead to electrolyte and fluid imbalances of the body tissues and cause reduced milk flow. This condition is commonly recognized by swine producers in the form of udder caking, mammary gland edema, reduced stool formation, and inappetence or anorexia.

Many treatments and management programs have been employed by swine producers and veterinarians to reduce the incidence and severity of lactation failure, agalactia, constipation, and udder edema in an effort to reduce piglet mortality. Bulk fibrous feedstuffs have been added to lactation rations to reduce constipation and udder edema. Unfortunately, the extensive use of these feedstuffs in the lactation ration reduces the caloric density of the ration which restricts the formation of blood sugars required for optimum milk flow. Other laxative agents have been employed in the form of potent chemicals that have a cathartic action. This cathartic action draws water into the bowel from body tissue reserves through osmotic activity. As the bowel expands with fluid, evacuation is initiated. Unfortunately, the extensive, prolonged use of chemicals leads to a chemical tolerance that requires continually higher levels or dosages of chemicals to achieve the desired response. As those dosage levels are increased, extensive fluids are lost via the bowels through the cathartic osmotic action. The continual loss of body fluid from the tissues leads to imbalances of the fluids and electrolytes which further contributes and predisposes the lactating sow to impaired milk production or agalactia.

The above treatments have been used to help alleviate the problem but the results have been inconsistent and not reliable. The lack of uniform responses has led to the use of a wide variety of management programs in an effort to reduce the mortality of piglets due to agalactia and constipation. Some management programs that have been used are restricting feed intake at farrowing time for 24 to 48 hours so as not to overload the digestive tract to precipitate indigestion. Another common practice is the feeding of antibiotics to hopefully reduce complications of bacterial infections which might otherwise result in mastitis and metritis which would further impede the production of milk. These practices have been used with some success; however, after extensive use for 10 to 20 years, the mortality rate of nursing piglets has not fallen significantly under average farm conditions.

The corrective actions employed to date, i.e., feeding of fibrous feedstuffs, use of chemical cathartics, antibiotics, and restrictive feeding have not significantly reduced the economic losses from agalactia to the swine producer.

Thus a need has arisen for a composition for the treatment of impaired lactation which overcomes the disadvantages of prior treatments while achieving reduced mortality rate in nursing piglets.

Thus, it is an object of the present invention to provide a novel composition for the treatment of impaired lactation.

It is further an object of the present invention to provide such a novel lactation treatment composition which is administered orally.

It is further an object of the present invention to provide such a novel lactation treatment composition which can be fed to mammals which are pregnant or lactating.

It is further an object of the present invention to provide such a novel lactation treatment composition which can be continuously fed without reducing caloric intake.

It is further an object of the present invention to provide such a novel lactation treatment composition which helps maintain the proper osmotic pressure of the blood and interstitial tissue fluid.

It is further an object of the present invention to provide such a novel lactation treatment composition which helps eliminate the problems of intestinal stasis or constipation.

These and further objects and advantages of the present invention will become clearer in light of the following detailed description of an illustrative embodiment of this invention.

DESCRIPTION

A treatment for impaired lactation according to the teachings of the present invention includes a composition which may be orally administered preferrably by mixing with the feed of the animal or top dressing the daily feed ration of the animal and is described specifically for the treatment of impaired lactation in swine. It can be appreciated that the treatment composition may be varied according to the teachings of the present invention for the treatment of impaired lactation in cattle and other species by a person skilled in the art after the teachings of the present invention become known.

The composition for treatment of impaired lactation according to the teachings of the present invention contains a combination of natural and chemical ingredients consisting of blood albumin meal, ground psyllium seed husks, and electrolytes such as potassium chloride, sodium bicarbonate, and magnesium sulfate in specific combination levels. Particularly, in its preferred form, the treatment composition of the present invention provides a daily intake of blood albumin meal in the range of 0.73 grams to 4.2 grams, ground psyllium seed in the range of 0.30 grams to 6.0 grams, and electrolytes in the range of 2.20 grams to 12.0 grams depending upon the amount of feed consumed. Specifically, in its most preferred form, the electrolytes of the treatment composition of the present invention provides a daily intake of potassium chloride in the range of 1.80 grams to 10.0 grams, sodium bicarbonate in the range of 0.20 grams to 1.0 gram, and magnesium sulfate in the range of 0.20 grams to 1.0 gram depending upon the amount of feed consumed.

Sows are normally limit-fed 4 to 6 pounds of feed ration during gestation so they do not become overweight during pregnancy which also contributres to agalactia. Feed intake is then increased by several pounds about 10 to 20 days prior to farrowing. Then the sows are fed free choice (all they will eat) during lactation to provide the needed energy for maximum milk production. In its most preferred form, 8 pounds of the treatment composition of the present invention is mixed in a ton of feed so as to get the desired response during gestation and lactation, when the feed intake increases from 3 to 5 fold (4 to 25 pounds), with palatability and efficacy and without problems of toxicity.

Now that the composition contents have been set forth, subtle features and advantages of the treatment composition of the present invention can be set forth and appreciated. Specifically, blood albumin meal is provided in the treatment composition of the present invention as a rich source of nutrients such as amino acids. Further, blood albumin provides a more balanced source of amino acids than other meals such as vegetable, soybean, or other seed meals. Amino acids play an important role in helping to provide optimum osmotic pressure in the tissue of the pig. As set forth hereinbefore, proper osmotic pressure of the blood and interstitial tissue fluid around the mammary gland alveoli is essential for optimum milk production. Thus, blood albumin of the treatment composition of the present invention helps insure that the osmotic pressure around the mammary gland alveoli is optimized for reducing and/or preventing impaired lactation.

Additionally, blood albumin of the treatment composition of the present invention can be readily digested to assimilate the nutrients contained therein. These assimilated nutrients help restore tissue health which is essential for optimum milk production and which may be under stress at farrowing time.

It should be appreciated that the concentration level of blood albumin meal has been optimized in the present invention to maximize the osmotic pressure and nutrient assimilation advantages and to maximize intake. Specifically, consumption or intake of the feed of the pig may be interfered with if the level of blood albumin meal is too high especially when administered as a top dressing. The treatment composition of the present invention then capitalizes on the increased milk production advantages of blood albumin without detrimentally affecting feed intake which reduces milk production as a result of reduced glucose and nutrient intake and digestion.

Constipation is directly related to indigestion and indigestion is directly related to appetite. Thus, constipation results in a loss of appetite reducing feed and water intake which is essential for optimum milk production. Psyllium seed is provided in the treatment composition of the present invention as a natural laxative and as an effective aid in the treatment of constipation. Particularly, an oily, mucilaginous mass is formed when psyllium seed comes in contact with water or fluid. Thus, when the treatment composition of the present invention including psyllium seed is ingested, an oily, mucilaginous mass is formed when the psyllium seed contacts the water and fluid normally found in the digestive tract and lubricates the digestive tract. This lubrication helps stimulate evacuation. It should then be noted that body fluids are not drawn from outside the digestive tract but rather the treatment composition of the present invention utilizes water and fluid normally present in the digestive tract. Therefore, psyllium seed is an efficacious ingredient for the purpose of treating and preventing constipation.

It should also be appreciated that psyllium seed can be orally administered at continuous, low levels in the sow's feed without adverse effects. Specifically, psyllium seed includes low levels of fiber and thus does not raise the fiber level of the feed to which it is administered or decrease the caloric density of the ration to which it is administered. As set forth hereinbefore, prior high fiber treatments for constipation decreased the caloric density of the sow's daily ration. The maximum energy is most important in stimulating milk flow in sows up to their genetic capacity and thus reduction in caloric density adversely effects milk production. Likewise, psyllium seed does not have the potential for harmful action like prior chemical laxatives since tolerances are not developed as in chemical laxatives which require continually higher levels or dosages to achieve the desired response. Similarly, psyllium seed contained in the treatment composition of the present invention is not prone to provide overstimulation of the sow or gilt as did prior lactation treatments ultilizing laxatives. Additionally, extensive loss of body fluid and electrolytes does not occur utilizing the treatment composition of the present invention as may occur when chemical laxatives are utilized. Furthermore, toxic action present in chemical laxatives do not occur utilizing the treatment composition of the present invention due to the natural laxative action of psyllium seed.

Thus, it can be appreciated that continuous administration of the treatment composition of the present invention can be had without predisposing the animal to lactation failure as in prior lactation treatments arising from decreased caloric intake, tolerance increases, toxicity, and the like. Further, administration of the treatment composition of the present invention decreases indigestion resulting in better appetite and in quicker and better digestion and assimilation of food and water for optimizing milk production.

Prior lactation treatments have had a generally narrower margin of safety than the treatment composition of the present invention when fed to pregnant sows or gilts, especially when they encounter enteric infections that lead to diarrhea and scours. Particularly, diarrhea and scours result in the loss of body fluids. This loss of body fluids is then compounded by prior chemical treatments which draw water into the bowel from body tissue reserves. It can then be appreciated that if a large inventory of feed with prior chemical treatments mixed within is on hand during an outbreak of an enteric disease causing diarrhea and/or scours, severe problems are encountered. On the other hand, since the treatment composition of the present invention does not draw water from body tissue reserves, it does not compound the effects of loss of body fluids caused by diarrhea and scours and may in fact help soothe the intestinal tract from irritation due to the oily, mucilaginous lubrication provided by the psyllium seed included in the treatment composition of the present invention. Further, the treatment composition of the present invention can be administered to pregnant sows or gilts without fear of inducing abortion of the fetuses.

The special electrolyte base of potassium chloride, sodium bicarbonate, and magnesium sulfate are provided in the treatment composition of the present invention at the prescribed rates to provide for electrolyte action to help eliminate fluid and electrolyte imbalances in the tissues that can lead to excessive udder edema and caking which contribute to agalactia or poor milk production. It should then be noted that the treatment composition of the present invention allows the electrolyte ions to be present at low, balanced levels with respect to each other so as not to provide an excess of any one ion at the expense of the other. An excessive amount of any one ion such as potassium may result in a bad taste which reduces palatability especially when administered as a top dressing and may further result in undesirable physiological reactions in the animal.

Likewise, if electrolytes are utilized at higher levels and especially for extensive periods of time, they frequently irritate the mucosa of the digestive tract to result in mild forms of irritation which can result in diarrhea and may produce a cathartic action. Thus, high levels of electrolytes may lead to agalactia.

Further, no salt (sodium chloride) has been added to the treatment composition of present invention for several reasons. First, an excessive amount of sodium may lead to tissue fluid retention and udder edema. Sodium is often present at high levels in water from many farm wells. Further, sodium is often present at adequate levels in most feed stuffs with which the treatment composition of the present invention is mixed. Thus, the treatment composition of the present invention does not include salt to avoid any potential compounding effects when mixed with water and feed already having high levels of sodium and which may lead to undesirable physiological damage. Further, salt also reduces palatability and thus the treatment composition of the present invention has greater palatability than prior treatment compositions.

A further understanding of the present invention can be had from the following examples of non-limiting field trials. For example, an extensive field trial on a farm that had a consistent history of problems with constipation and udder edema resulting in agalactia produced the following results:

|  | Treated Sows | Untreated Sows |
|---|---|---|
| Scoring on stool consistency | 4.3 | 3.3 |
| Scoring on udder caking | 4.6 | 4.0 |
| Scoring on appetite | 4.3 | 2.0 |

| Stool Consistency | Udder Caking |
|---|---|
| 1 Extreme constipation | 1 Extreme caking throughout udder |
| 2 Above average constipation problems | 2 Mild caking throughout udder |
| 3 Some persistent constipation | 3 Several caked nipples at farrowing |
| 4 Intermittent constipation | 4 Slight caking at farrowing |
| 5 Desireable stool | 5 Normal udder |

| Appetite |
|---|
| 1 Poor appetite |
| 2 Below average feed intake |
| 3 Average feed intake |
| 4 Above average feed intake |
| 5 Very good feed consumption |

The results of this trial clearly indicate the value of the treatment composition of the present invention.

Likewise, another field trial produced the following results:

| Treated Sows | | | | | |
|---|---|---|---|---|---|
| Sow Number | Pigs Farrowed | Litter Farrowing Weight | Average Pig Birth Weight | Pigs Weaned | Litter Weaning Weight | Average Pig Weaning Weight |
| 18 | 11 | 37 | 3.3 | 11 | 138 | 12.5 |
| 28 | 8 | 24 | 3.0 | 8 | 159 | 19.8 |
| 38 | 9 | 31 | 3.4 | 7 | 119 | 17.0 |
| 45 | 10 | 28 | 2.8 | 9 | 76 | 8.4 |
| 55 | 11 | 33 | 3.0 | 9 | 132 | 14.6 |
| 65 | 9 | 29 | 3.2 | 9 | 118 | 13.1 |
| 78 | 9 | 28 | 3.1 | 8 | 96 | 12.0 |
| 85 | 9 | 29 | 3.2 | 8 | 123 | 15.3 |
| Total | 76 | 239 |  | 69 | 961 |  |
| Average | 9.5 | 29.8 | 3.1 | 8.6 | 120.1 | 13.9 |

| Untreated Sows | | | | | |
|---|---|---|---|---|---|
| Sow Number | Pigs Farrowed | Litter Farrowing Weight | Average Pig Birth Weight | Pigs Weaned | Litter Weaning Weight | Average Pig Weaning Weight |
| 1 | 11 | 30 | 2.7 | 6 | 85 | 14.1 |
| 2 | 9 | 32 | 3.5 | 9 | 110 | 12.2 |
| 3 | 11 | 34 | 3.1 | 11 | 146 | 13.2 |
| 4 | 9 | 29 | 3.2 | 8 | 111 | 13.8 |
| 6 | 10 | 34 | 3.4 | 10 | 117 | 11.7 |
| 7 | 9 | 30 | 3.3 | 7 | 113 | 16.1 |
| 10 | 11 | 34 | 3.1 | 11 | 140 | 12.7 |
| Total | 70 | 223 |  | 62 | 822 |  |
| Average | 10 | 31.8 | 3.2 | 8.8 | 117.1 | 13.3 |

The above field trial illustrates the improvement in lactation resulting from the administration of the treatment composition of the present invention since the differential between average weaning weights between the piglets of the treated and untreated sows was 0.7 lbs. It was also observed that sows receiving the treatment composition of the present invention had better appetites with less problems of constipation. It can then be appreciated that the treatment composition according to the teachings of the present invention reduced constipation, increased appetite, and reduced udder caking producing healthier, heavier piglets as compared to sows not treated with the present invention.

The treatment composition of the present invention provides for a slow, gentle anticonstipating action in a palatable manner maintaining a good appetite with less signs of constipation while maintaining optimum milk production with less signs of udder edema and caking. Particularly, the selection, combination, and levels of blood albumin meal, psyllium seed, and the electrolyte base results in a unique and effective treatment of impaired lactation which surpasses prior treatments. Specifically, the treatment composition of the present invention provides a very high level of nutrients that can be quickly assimilated after ingestion, with the quick assimilation not being interfered with by other ingredients present in the treatment composition of the present invention. This quick assimilation helps promote the proper osmotic balance essential for optimum milk production. Further, the treatment composition of the present invention provides a natural anticonstipation agent which does not irritate the digestive tract or otherwise interfere with digestion and assimilation of the water and feed, reduce caloric density of the feed ration, cause problems of proper tissue fluid and osmotic balance, or result in problems of developing chemical tolerances. With reduced constipation encountered in lactating sows, the sows have less indigestion resulting in better appetites. With better appetites, greater intake of feed, water, and treatment composition occurs providing the nutrients, electrolytes, and fluid necessary for optimum milk production. Furthermore, the treatment composition of the present invention includes an electrolyte base to help eliminate fluid and electrolyte imbalance. Additionally, the treatment composition of the present invention is extremely palatable to increase consumption of the treatment composition and the feed with which it is mixed. Therefore, the treatment composition of the present invention can be continuously fed over extended periods of time to both pregnant and lactating sows and gilts without encountering the numerous disadvantages of prior treatments.

It should then be appreciated that the treatment composition according to the teachings of the present invention are an effective aid in the prevention and treatment of constipation in lactating sows and gilts, udder edema (caking as a result of electrolyte and fluid imbalances), and anorexia and inappetence in the newly farrowed gilt and sow. Further, as the result of better appetite and quick and better digestion and assimilation of the food and water, udder development is naturally stimulated to its genetic capacity. Thus, milk production is optimized for the genetic capacity of the sows and gilts administered the treatment composition of the present invention. Optimum milk production results in well-nourished, strong and healthy piglets having a reduced mortality rate.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalency of the claims are intended to be embraced therein.

What is claimed is:

1. An orally administered composition as a nutritional aid for the treatment of impaired lactation and for obtaining optimum milk production in swine comprising: and amount of ground psyllium seed husks; an amount of blood albumin meal; and electrolytes, with the composition stimulating evacuation of the digestive tract without drawing fluids from outside the digestive tract wherein the administration thereof to said swine provides a daily intake of electrolytes in the range of 2.20 to 2.0 grams.

2. An orally administered composition as a nutritional aid for the treatment of impaired lactation and for obtaining optimum milk production in swine comprising: an amount of psyllium seed husks; an amount of blood albumun meal; and electrolytes; said electrolytes being free of sodium chloride; said composition stimulating evacuation of the digestive tract without drawing fluids from outside the digestive tract wherein the administration thereof to said swine provides a daily intake of psyllium seed in the range of 0.30 to 6.0 grams; a daily intake of blood albumin meal in the range of 0.73 to 4.2 grams and a daily intake of electrolytes in the range of 2.20 to 2.0 grams.

3. The treatment composition of claim 2 wherein the electrolytes comprise: potassium chloride, sodium bicarbonate, and magnesium sulfate.

4. The treatment composition of claim 3 wherein the daily intake of potassium chloride is in the range of 1.80 to 10 grams, the daily intake of sodium bicarbonate is in the range of 0.20 to 1 gram, and the daily intake of magnesium sulfate is in the range of 0.20 to 1 gram.

5. The treatment composition of claim 2 wherein the treatment composition is adapted for oral administration by mixing with feed.

6. The treatment composition of claim 2 wherein the treatment composition is adapted for oral administration by top dressing a feed.

7. The treatment composition of claim 6 wherein the electrolytes comprise: potassium chloride, sodium bicarbonate, and magnesium sulfate.

8. The treatment composition of claim 7 wherein the daily intake of potassium chloride is in the range of 1.80 to 10 grams, the daily intake of sodium bicarbonate is in the range of 0.20 to 1 gram, and the daily intake of magnesium sulfate is in the range of 0.20 to 1 gram.

9. The treatment composition of claim 5 wherein the electrolytes comprise: potassium chloride, sodium bicarbonate, and magnesium sulfate.

10. The treatment composition of claim 9 wherein the daily intake of potassium chloride is in the range of 1.80 to 10 grams, the daily intake of sodium bicarbonate is in the range of 0.20 to 1 gram, and the daily intake of magnesium sulfate is in the range of 0.20 to 1 gram.

11. A method for treating the impaired lactation in swine comprising orally administering the composition defined in claim 1 to swine having need thereof.

* * * * *